United States Patent
Bonnefin et al.

(10) Patent No.: US 10,968,543 B2
(45) Date of Patent: Apr. 6, 2021

(54) WOUND DRESSING FOR USE IN VACUUM THERAPY

(71) Applicant: CONVATEC TECHNOLOGIES INC., Las Vegas, NV (US)

(72) Inventors: Wayne Bonnefin, Clwyd (GB); Sarah Wroe, Clwyd (GB); Amelia Prentice, Clwyd (GB)

(73) Assignee: CONVATEC TECHNOLOGIES INC., Las Vegas, NV (US)

( * ) Notice: Subject to any disclaimer, the term of this patent is extended or adjusted under 35 U.S.C. 154(b) by 438 days.

(21) Appl. No.: 14/362,039

(22) PCT Filed: Nov. 29, 2012

(86) PCT No.: PCT/GB2012/052950
§ 371 (c)(1),
(2) Date: May 30, 2014

(87) PCT Pub. No.: WO2013/079947
PCT Pub. Date: Jun. 6, 2013

(65) Prior Publication Data
US 2014/0323999 A1    Oct. 30, 2014

(30) Foreign Application Priority Data
Dec. 1, 2011    (GB) .................................... 1120693

(51) Int. Cl.
*A61F 13/00*    (2006.01)
*D02G 3/04*    (2006.01)
(Continued)

(52) U.S. Cl.
CPC ......... *D02G 3/04* (2013.01); *A61F 13/00012* (2013.01); *A61F 13/00021* (2013.01);
(Continued)

(58) Field of Classification Search
CPC .......... A61F 13/00021; A61F 13/00068; A61F 13/00012; A61F 13/00063; A61F 13/0209;
(Continued)

(56) References Cited

U.S. PATENT DOCUMENTS 4,984,570 A * 1/1991 Langen ............ A61F 13/00008
602/44
5,731,083 A    3/1998 Bahia et al.
(Continued)

FOREIGN PATENT DOCUMENTS

CN    1307489 A    8/2001
EP    0525062 A1    2/1993
(Continued)

OTHER PUBLICATIONS

Australian Patent Application No. 2012343581 Examiner's Second Report dated Jun. 27, 2016.
(Continued)

*Primary Examiner* — Kai H Weng
(74) *Attorney, Agent, or Firm* — Taft Stettinius & Hollister LLP; Ryan O. White

(57) ABSTRACT

A wound dressing for use in vacuum wound therapy comprising a wound contact layer which is an open structure comprising a yarn comprising gel-forming filaments or fibres, the structure having a porosity which allows exudate to flow through it.

20 Claims, 7 Drawing Sheets

(51) Int. Cl.
*D04B 21/12* (2006.01)
*A61L 15/42* (2006.01)
*A61L 15/60* (2006.01)
*D06M 13/21* (2006.01)
*D06M 23/10* (2006.01)
*A61F 13/02* (2006.01)
*D02G 3/44* (2006.01)
*D01G 15/00* (2006.01)
*D01H 4/10* (2006.01)
*D02G 3/02* (2006.01)
*D06B 9/00* (2006.01)
*D06M 101/06* (2006.01)

(52) U.S. Cl.
CPC .. *A61F 13/00063* (2013.01); *A61F 13/00068* (2013.01); *A61F 13/0209* (2013.01); *A61L 15/425* (2013.01); *A61L 15/60* (2013.01); *D01G 15/00* (2013.01); *D01H 4/10* (2013.01); *D02G 3/02* (2013.01); *D02G 3/448* (2013.01); *D04B 21/12* (2013.01); *D06B 9/00* (2013.01); *D06M 13/21* (2013.01); *D06M 23/10* (2013.01); *A61F 2013/0054* (2013.01); *A61F 2013/00174* (2013.01); *A61F 2013/00229* (2013.01); *A61F 2013/00242* (2013.01); *A61F 2013/00536* (2013.01); *D06M 2101/06* (2013.01); *D10B 2509/022* (2013.01); *Y10T 428/2975* (2015.01)

(58) Field of Classification Search
CPC .. A61F 2013/00174; A61F 2013/00229; A61F 2013/00242; A61F 2013/00536; A61F 2013/0054; D02G 3/02; D02G 3/448; D10B 2509/022; A61L 15/425; A61L 15/60
See application file for complete search history.

(56) References Cited

U.S. PATENT DOCUMENTS

| | | | |
|---|---|---|---|
| 6,268,544 B1 * | 7/2001 | Court | A61F 13/00008 602/41 |
| 6,458,460 B1 | 10/2002 | Griffiths et al. | |
| 6,471,982 B1 | 10/2002 | Lydon et al. | |
| 6,548,730 B1 | 4/2003 | Patel et al. | |
| 6,656,496 B1 * | 12/2003 | Kilpadi | A61L 27/18 424/422 |
| 7,951,124 B2 | 5/2011 | Boehringer et al. | |
| 10,016,537 B2 | 7/2018 | Menon et al. | |
| 10,046,096 B2 | 8/2018 | Askem et al. | |
| 10,076,447 B2 | 9/2018 | Barta et al. | |
| 10,143,784 B2 | 12/2018 | Walton et al. | |
| 10,426,670 B2 | 10/2019 | von Blucher et al. | |
| 10,426,747 B2 | 10/2019 | Johnson | |
| 10,426,875 B2 | 10/2019 | Blott et al. | |
| 10,434,015 B2 | 10/2019 | Taylor et al. | |
| 10,434,142 B2 | 10/2019 | Niazi et al. | |
| 10,434,210 B2 | 10/2019 | Olson et al. | |
| 10,434,284 B2 | 10/2019 | Hanson et al. | |
| D866,756 S | 11/2019 | Allen et al. | |
| 10,463,773 B2 | 11/2019 | Haggstrom et al. | |
| 10,470,933 B2 | 11/2019 | Riesinger | |
| 10,470,936 B2 | 11/2019 | Wohlgemuth et al. | |
| 10,473,345 B2 | 11/2019 | Barta et al. | |
| 10,485,707 B2 | 11/2019 | Sexton | |
| 10,485,906 B2 | 11/2019 | Freedman et al. | |
| 10,492,956 B2 | 12/2019 | Zamierowski | |
| 10,493,184 B2 | 12/2019 | Collinson et al. | |
| 10,493,185 B2 | 12/2019 | Stokes et al. | |
| 10,500,103 B2 | 12/2019 | Crolzat et al. | |
| 10,500,173 B2 | 12/2019 | Yang et al. | |
| 10,500,301 B2 | 12/2019 | Laurensou | |
| 10,500,302 B2 | 12/2019 | Holm et al. | |
| 10,506,928 B2 | 12/2019 | Locke et al. | |
| 10,507,141 B2 | 12/2019 | Allen et al. | |
| 10,532,137 B2 | 1/2020 | Pratt et al. | |
| 10,532,194 B2 | 1/2020 | Locke et al. | |
| 10,537,657 B2 | 1/2020 | Phillips et al. | |
| 10,542,936 B2 | 1/2020 | Goldberg et al. | |
| 10,543,133 B2 | 1/2020 | Shaw et al. | |
| 10,543,293 B2 | 1/2020 | Suschek | |
| 10,555,838 B2 | 2/2020 | Wu et al. | |
| 10,555,839 B2 | 2/2020 | Hartwell | |
| 10,556,044 B2 | 2/2020 | Robinson et al. | |
| 10,561,536 B2 | 2/2020 | Holm et al. | |
| 10,568,767 B2 | 2/2020 | Addison et al. | |
| 10,568,768 B2 | 2/2020 | Long et al. | |
| 10,568,771 B2 | 2/2020 | MacDonald et al. | |
| 10,576,037 B2 | 3/2020 | Harrell | |
| 10,576,189 B2 | 3/2020 | Locke et al. | |
| 10,589,007 B2 | 3/2020 | Coulthard et al. | |
| 10,610,415 B2 | 4/2020 | Griffey et al. | |
| 10,610,623 B2 | 4/2020 | Robinson et al. | |
| 10,618,266 B2 | 4/2020 | Wright et al. | |
| 10,624,984 B2 | 4/2020 | Courage et al. | |
| 10,625,002 B2 | 4/2020 | Locke et al. | |
| 10,632,019 B2 | 4/2020 | Vitaris | |
| 10,632,224 B2 | 4/2020 | Hardy et al. | |
| 10,639,206 B2 | 5/2020 | Hu et al. | |
| 10,639,404 B2 | 5/2020 | Lichtenstein | |
| 10,653,562 B2 | 5/2020 | Robinson et al. | |
| 10,653,810 B2 | 5/2020 | Datt et al. | |
| 10,653,823 B2 | 5/2020 | Bharti et al. | |
| 10,660,799 B2 | 5/2020 | Wu et al. | |
| 10,660,992 B2 | 5/2020 | Canner et al. | |
| 10,660,994 B2 | 5/2020 | Askem et al. | |
| 10,667,955 B2 | 6/2020 | Allen et al. | |
| 10,667,956 B2 | 6/2020 | Van Holten et al. | |
| 10,682,258 B2 | 6/2020 | Manwaring et al. | |
| 10,682,259 B2 | 6/2020 | Hunt et al. | |
| 10,682,318 B2 | 6/2020 | Twomey et al. | |
| 10,682,386 B2 | 6/2020 | Ellis-Behnke et al. | |
| 10,687,983 B2 | 6/2020 | Dahlberg et al. | |
| 10,687,985 B2 | 6/2020 | Lee et al. | |
| 10,688,215 B2 | 6/2020 | Munro et al. | |
| 10,688,217 B2 | 6/2020 | Hanson et al. | |
| 10,744,040 B2 | 6/2020 | Kazala, Jr. et al. | |
| RE48,117 E | 7/2020 | Albert et al. | |
| 10,702,419 B2 | 7/2020 | Locke et al. | |
| 10,702,420 B2 | 7/2020 | Hammond et al. | |
| 10,703,942 B2 | 7/2020 | Tunius | |
| 10,709,760 B2 | 7/2020 | Gronberg et al. | |
| 10,709,883 B2 | 7/2020 | Spector | |
| 10,716,711 B2 | 7/2020 | Locke et al. | |
| 10,716,874 B2 | 7/2020 | Koyama et al. | |
| 10,729,590 B2 | 8/2020 | Simmons et al. | |
| 10,736,787 B2 | 8/2020 | Hannigan et al. | |
| 10,736,788 B2 | 8/2020 | Locke et al. | |
| 10,736,985 B2 | 8/2020 | Odermatt et al. | |
| 10,743,900 B2 | 8/2020 | Ingram et al. | |
| 10,744,041 B2 | 8/2020 | Hartwell | |
| 10,744,237 B2 | 8/2020 | Guidi et al. | |
| 10,744,238 B2 | 8/2020 | Guidi et al. | |
| 10,744,240 B2 | 8/2020 | Simmons et al. | |
| 10,751,442 B2 | 8/2020 | Bonnefin et al. | |
| 10,751,452 B2 | 8/2020 | Topaz | |
| 10,758,423 B2 | 9/2020 | Pigg et al. | |
| 10,758,424 B2 | 9/2020 | Blott et al. | |
| 10,758,425 B2 | 9/2020 | Blott et al. | |
| 10,758,426 B2 | 9/2020 | Eddy | |
| 10,758,651 B2 | 9/2020 | Blott et al. | |
| 10,765,561 B2 | 9/2020 | Lattimore et al. | |
| 10,765,783 B2 | 9/2020 | Locke et al. | |
| 10,772,767 B2 | 9/2020 | Bjork et al. | |
| 10,780,203 B2 | 9/2020 | Coulthard et al. | |
| 10,792,191 B2 | 10/2020 | Robinson et al. | |
| 10,792,192 B2 | 10/2020 | Tout et al. | |
| 10,792,337 B2 | 10/2020 | Leung et al. | |
| 10,792,404 B2 | 10/2020 | Hu et al. | |
| 10,792,482 B2 | 10/2020 | Randolph et al. | |
| 2002/0129596 A1 | 9/2002 | Driggars | |

(56) References Cited

U.S. PATENT DOCUMENTS

| | | |
|---|---|---|
| 2006/0155260 A1 | 7/2006 | Blott et al. |
| 2006/0172000 A1 | 8/2006 | Cullen et al. |
| 2007/0066945 A1 | 3/2007 | Martin et al. |
| 2007/0185426 A1 | 8/2007 | Ambrosio et al. |
| 2007/0219512 A1 | 9/2007 | Heaton et al. |
| 2007/0225663 A1 | 9/2007 | Watt et al. |
| 2007/0239078 A1 | 10/2007 | Jaeb |
| 2009/0234307 A1 | 9/2009 | Vitaris |
| 2009/0259203 A1 | 10/2009 | Hu et al. |
| 2009/0293887 A1 | 12/2009 | Wilkes et al. |
| 2009/0299303 A1 | 12/2009 | Seegert |
| 2010/0015208 A1 | 1/2010 | Kershaw et al. |
| 2010/0030178 A1 | 2/2010 | MacMeccan et al. |
| 2010/0042034 A1 | 2/2010 | Riesinger |
| 2010/0125233 A1 | 5/2010 | Edward et al. |
| 2010/0125258 A1 | 5/2010 | Coulthard et al. |
| 2010/0137775 A1 | 6/2010 | Hu et al. |
| 2010/0185163 A1 | 7/2010 | Heagle |
| 2010/0298790 A1 | 11/2010 | Guidi et al. |
| 2011/0015595 A1 | 1/2011 | Robinson et al. |
| 2011/0028918 A1 | 2/2011 | Hartwell |
| 2011/0112457 A1 | 5/2011 | Holm et al. |
| 2011/0178451 A1 | 7/2011 | Robinson et al. |
| 2011/0213319 A1* | 9/2011 | Blott .................. A61M 3/0283 604/291 |
| 2011/0224593 A1 | 9/2011 | Tunius |
| 2011/0224630 A1 | 9/2011 | Simmons et al. |
| 2011/0230849 A1 | 9/2011 | Coulthard et al. |
| 2011/0251566 A1 | 10/2011 | Zimnitsky et al. |
| 2011/0257572 A1 | 10/2011 | Locke et al. |
| 2011/0257573 A1 | 10/2011 | Hong et al. |
| 2011/0275972 A1 | 11/2011 | Rosenberg |
| 2011/0282309 A1 | 11/2011 | Adie et al. |
| 2012/0071845 A1 | 3/2012 | Hu et al. |
| 2012/0130332 A1 | 5/2012 | Cotton et al. |
| 2012/0136325 A1 | 5/2012 | Allen et al. |
| 2012/0209226 A1 | 8/2012 | Simmons et al. |
| 2012/0276183 A1 | 11/2012 | Bradford |
| 2013/0053795 A1 | 2/2013 | Coulthard et al. |
| 2013/0123728 A1 | 5/2013 | Pratt et al. |
| 2013/0226063 A1 | 8/2013 | Taylor et al. |
| 2014/0005618 A1 | 1/2014 | Locke et al. |
| 2014/0074053 A1 | 3/2014 | Locke et al. |
| 2014/0188060 A1 | 7/2014 | Robinson et al. |
| 2014/0194838 A1 | 7/2014 | Wibaux et al. |
| 2014/0200532 A1 | 7/2014 | Robinson et al. |
| 2014/0236112 A1 | 8/2014 | Von Wolff et al. |
| 2014/0256925 A1 | 9/2014 | Catchmark et al. |
| 2014/0276499 A1 | 9/2014 | Locke et al. |
| 2014/0296804 A1 | 10/2014 | Hicks et al. |
| 2014/0308338 A1 | 10/2014 | Nierle et al. |
| 2014/0309574 A1 | 10/2014 | Cotton |
| 2014/0323999 A1 | 10/2014 | Bonnefin et al. |
| 2015/0018433 A1 | 1/2015 | Leipzig et al. |
| 2015/0057624 A1 | 2/2015 | Simmons et al. |
| 2015/0071985 A1 | 3/2015 | Walker et al. |
| 2015/0079152 A1 | 3/2015 | Wuollett et al. |
| 2015/0094674 A1 | 4/2015 | Pratt et al. |
| 2015/0104486 A1 | 4/2015 | Bonnefin et al. |
| 2015/0112311 A1 | 4/2015 | Hammond et al. |
| 2015/0119831 A1 | 4/2015 | Robinson et al. |
| 2015/0119834 A1 | 4/2015 | Locke et al. |
| 2015/0141941 A1 | 5/2015 | Allen et al. |
| 2015/0148785 A1 | 5/2015 | Kleiner |
| 2015/0174304 A1 | 6/2015 | Askem et al. |
| 2015/0245949 A1 | 9/2015 | Locke et al. |
| 2015/0246164 A1 | 9/2015 | Heaton et al. |
| 2015/0250979 A1 | 9/2015 | Loske |
| 2015/0265741 A1 | 9/2015 | Duncan et al. |
| 2015/0265743 A1 | 9/2015 | Hanson et al. |
| 2015/0320901 A1 | 11/2015 | Chandrashekhar-Bhat et al. |
| 2016/0008293 A1 | 1/2016 | Shi et al. |
| 2016/0051724 A1 | 2/2016 | Sahin et al. |
| 2016/0067107 A1 | 3/2016 | Cotton |
| 2016/0100987 A1 | 4/2016 | Hartwell et al. |
| 2016/0106878 A1 | 4/2016 | Yang et al. |
| 2016/0106892 A1 | 4/2016 | Hartwell |
| 2016/0166422 A1 | 6/2016 | Karim et al. |
| 2016/0193244 A1 | 7/2016 | Ota et al. |
| 2016/0222548 A1 | 8/2016 | Agboh |
| 2016/0271178 A1 | 9/2016 | Hauser et al. |
| 2016/0287743 A1 | 10/2016 | Andrews |
| 2017/0049111 A1 | 2/2017 | Patton et al. |
| 2017/0189237 A1 | 7/2017 | Locke et al. |
| 2019/0293881 A1 | 10/2019 | Ramjit et al. |
| 2019/0298577 A1 | 10/2019 | Locke et al. |
| 2019/0298578 A1 | 10/2019 | Shulman et al. |
| 2019/0298582 A1 | 10/2019 | Addison et al. |
| 2019/0307611 A1 | 10/2019 | Askem et al. |
| 2019/0307612 A1 | 10/2019 | Hartwell et al. |
| 2019/0307934 A1 | 10/2019 | Allen et al. |
| 2019/0314209 A1 | 10/2019 | Ha et al. |
| 2019/0321509 A1 | 10/2019 | Chakravarthy et al. |
| 2019/0321526 A1 | 10/2019 | Robinson et al. |
| 2019/0336641 A1 | 11/2019 | Nisbet |
| 2019/0336658 A1 | 11/2019 | Heaton et al. |
| 2019/0336739 A1 | 11/2019 | Locke et al. |
| 2019/0343979 A1 | 11/2019 | Kearney et al. |
| 2019/0343993 A1 | 11/2019 | Weston |
| 2019/0343994 A1 | 11/2019 | Greener |
| 2019/0350763 A1 | 11/2019 | Pratt et al. |
| 2019/0350765 A1 | 11/2019 | Heagle et al. |
| 2019/0351111 A1 | 11/2019 | Locke et al. |
| 2019/0358361 A1 | 11/2019 | McInnes et al. |
| 2019/0374408 A1 | 12/2019 | Robles et al. |
| 2019/0374673 A1 | 12/2019 | Hoefinghoff et al. |
| 2019/0380881 A1 | 12/2019 | Albert et al. |
| 2019/0380882 A1 | 12/2019 | Taylor et al. |
| 2019/0380883 A1 | 12/2019 | MacPhee et al. |
| 2019/0381222 A9 | 12/2019 | Locke et al. |
| 2019/0388577 A1 | 12/2019 | Chandrashekhar-Bhat et al. |
| 2019/0388579 A1 | 12/2019 | MacPhee et al. |
| 2019/0388589 A1 | 12/2019 | MacPhee et al. |
| 2020/0022844 A1 | 1/2020 | Blott et al. |
| 2020/0023103 A1 | 1/2020 | Joshi et al. |
| 2020/0030499 A1 | 1/2020 | Menon et al. |
| 2020/0038023 A1 | 2/2020 | Dunn |
| 2020/0038639 A1 | 2/2020 | Patel et al. |
| 2020/0046565 A1 | 2/2020 | Barta et al. |
| 2020/0046568 A1 | 2/2020 | Sexton |
| 2020/0061254 A1 | 2/2020 | Joshi et al. |
| 2020/0069835 A1 | 3/2020 | Hissink et al. |
| 2020/0069851 A1 | 3/2020 | Blott et al. |
| 2020/0078225 A1 | 3/2020 | Grillitsch et al. |
| 2020/0085626 A1 | 3/2020 | Braga et al. |
| 2020/0085630 A1 | 3/2020 | Robinson et al. |
| 2020/0100945 A1 | 4/2020 | Albert et al. |
| 2020/0113741 A1 | 4/2020 | Rehbein et al. |
| 2020/0114049 A1 | 4/2020 | Wall |
| 2020/0129675 A1 | 4/2020 | Robinson et al. |
| 2020/0138754 A1 | 5/2020 | Johnson |
| 2020/0139023 A1 | 5/2020 | Haggstrom et al. |
| 2020/0146894 A1 | 5/2020 | Long et al. |
| 2020/0155379 A1 | 5/2020 | Shaw et al. |
| 2020/0170843 A1 | 6/2020 | Collinson et al. |
| 2020/0171197 A1 | 6/2020 | Hubbell et al. |
| 2020/0254139 A1 | 8/2020 | Phillips et al. |
| 2020/0261275 A1 | 8/2020 | Manwaring et al. |
| 2020/0276055 A1 | 9/2020 | Randolph et al. |
| 2020/0297894 A1 | 9/2020 | Koyama et al. |
| 2020/0299865 A1 | 9/2020 | Bonnefin et al. |
| 2020/0306091 A1 | 10/2020 | Lee et al. |
| 2020/0315854 A1 | 10/2020 | Simmons et al. |
| 2020/0330283 A1 | 10/2020 | Locke et al. |
| 2020/0330284 A1 | 10/2020 | Locke et al. |
| 2020/0337719 A1 | 10/2020 | Ingram et al. |

FOREIGN PATENT DOCUMENTS

| | | |
|---|---|---|
| JP | 2000510539 A | 8/2000 |
| JP | 2003510475 A | 3/2003 |
| JP | 2006110393 A | 4/2006 |
| JP | 2008518726 A | 6/2008 |
| JP | 2008529618 A | 8/2008 |

(56) References Cited

FOREIGN PATENT DOCUMENTS

| | | |
|---|---|---|
| JP | 2011504127 A | 2/2011 |
| WO | WO-9116490 | 10/1991 |
| WO | WO-9312275 A1 | 6/1993 |
| WO | WO-9519795 A1 | 7/1995 |
| WO | WO-1998-046818 | 10/1998 |
| WO | WO-1999-064080 | 12/1999 |
| WO | WO-2000-001425 | 1/2000 |
| WO | WO-2001-023653 | 4/2001 |
| WO | 2005013543 A2 | 3/2005 |
| WO | WO-2006052839 A2 | 5/2006 |
| WO | WO-2006087021 A1 | 8/2006 |
| WO | WO-2010085426 A1 | 7/2010 |
| WO | WO-2010122665 A1 | 10/2010 |
| WO | WO-2011077096 A1 | 6/2011 |
| WO | 2011121394 A1 | 10/2011 |
| WO | 2011135284 A1 | 11/2011 |
| WO | 2011144888 A1 | 11/2011 |
| WO | 2013015827 A2 | 1/2013 |
| WO | WO-2013079947 A1 | 6/2013 |
| WO | WO-2013079949 A1 | 6/2013 |
| WO | 2013126049 A1 | 8/2013 |
| WO | 2014014842 A1 | 1/2014 |
| WO | 2015145117 A1 | 10/2015 |
| WO | 2015173546 A1 | 11/2015 |

OTHER PUBLICATIONS

Australian Patent Application No. 2012343583 Patent Examination Report No. 1 dated Aug. 10, 2016.
Chinese Patent Application No. 201280068356.8 First Office Action dated Jun. 8, 2015.
Chinese Patent Application No. 201280068356.8 Second Office Action dated Apr. 18, 2016.
Chinese Patent Application No. 201280068502.7 First Office Action dated Sep. 6, 2015.
Chinese Patent Application No. 201280068502.7 Second Office Action dated Jun. 15, 2016.
Colombia Patent Application No. 14-139575-8 Writ dated Jun. 1, 2016.
Columbia Patent Application No. 14-139580 Writ dated Jun. 1, 2016.
PCT/GB2012/052950 International Preliminary Report on Patentability dated Jun. 3, 2014.
PCT/GB2012/052952 International Preliminary Report on Patentability dated Jun. 3, 2014.
PCT/GB2012/052952 International Search Report dated Mar. 1, 2013.
U.S. Appl. No. 14/362,050 Office Action dated Apr. 29, 2015.
U.S. Appl. No. 14/362,050 Office Action dated Feb. 10, 2016
Karamuk, E., et al., "TISSUPOR: Development of a structured wound dressing based on a textile composite functionalised by embroidery technology," KTI. Projekt No. 511, (2001), XP55054592, available from: URL:http://www.tissupor.com/pdf/tissupor_kti.pdf.
PCT-GB-2012-052950 International Search Report dated Feb. 28, 2013.
Australian Patent Application No. 2012343583 Examiner's First Report dated Aug. 10, 2016.
Chinese Patent Application No. 201280068356.8 Third Office Action dated Oct. 25, 2016.
Chinese Patent Application No. 201280068502.7 Third Office Action dated Feb. 4, 2017.
Colombia Patent Application No. 14-139575 Writ No. 11665 dated Oct. 19, 2016 (in Spanish) with foreign associate reporting letter dated Nov. 3, 2016 (in English).
Colombia Patent Application No. 14-139850 Writ dated Oct. 12, 2016.
European Patent Application No. 12798352.6 Communication dated Aug. 29, 2016.
Japanese Patent Application No. 2014-543971 Office Action dated Nov. 29, 2016.
Japanese Patent Application No. 2014-543972 Office Action dated Dec. 20, 2016.
New Zealand Patent Application No. 626695 Further Examination Report dated Sep. 9, 2016.
New Zealand Patent Application No. 723782 Examiner's First Report dated Sep. 9, 2016.
Chinese Patent Application No. 201280028356.8 Office Action dated May 26, 2017.
Columbia Patent Application No. 14139575 Resolution No. 28622 dated May 23, 2017.
Guha et al., Predicting yarn tenacity: A comparison of mechanistic, statistical, and neural network models. The Journal of Textile Institute, 92(Issue 2, Parts 1 and 2):4 pages, 2001. Abstract.
Ramey et al., Relationship of cotton fiber properties to yarn tenacity. Textile Research Journal, 2 pages, Jul. 2, 2016. Abstract.
Japanese Patent Application No. 2014-543971 Office Action dated Aug. 1, 2017.
Chinese Patent Application No. 201280068356.8 Office Action dated May 3, 2018.
European Patent Application No. 18162727.4 Extended European Search Report dated Aug. 6, 2018.
Japanese Opposition No. 2018-700440 Decision of Opposition to Patent dated Oct. 5, 2018.
Japanese Opposition No. 2018-700440 Notice of Opposition to Patent dated May 30, 2018.
Korean Patent Application No. 10-2014-7017863 Office Action dated Aug. 10, 2018.

\* cited by examiner

WOUND DRESSING FOR USE IN VACUUM THERAPY

CROSS-REFERENCE

This application is a U.S. National Stage of PCT/GB2012/052950, filed Nov. 29, 2012; which claims the benefit of priority of GB1120693.5; filed Dec. 1, 2011; each of which is incorporated herein be reference in their entirety.

The present invention relates to a device and kit for treating a wound with a dressing and vacuum.

Vacuum has been used to increase blood flow to wound tissue and to remove exudate from the wound site. In general vacuum treatment uses a device comprising a cover for sealing about the outer perimeter of the wound, under which a vacuum is established to act on the wound surface. The vacuum applied to the wound surface accelerates healing of chronic wounds. A screen of open cell foam material or gauze is typically used under the cover to provide the space in which the vacuum is formed and to reduce tissue ingrowth. Sufficient vacuum is applied for a suitable duration to promote tissue migration in order to facilitate the closure of the wound. Suitable vacuum is between about 0.1 and 0.99 atmospheres. The vacuum can be substantially continuous or can be cyclic with the application of vacuum for alternating periods of application and nonapplication.

Many common conventional and advanced wound contact dressings have shortcomings particularly for use in suction wound therapy. In an example, gauze and other similar flat fabric materials are commonly used as wound dressings. When gauze is in contact with a wound it becomes wet with exudate and collapses into the wound. New tissue growth can engulf the gauze making it difficult and painful to remove from the wound. When foam is in contact with a wound and vacuum is applied, the foam can collapse and in-growth of tissue can occur into the collapsed cell structure of the foam. In order to overcome this problem relatively rigid perforated sheets have been used to contact the wound. However, they are not sufficiently flexible and conformable to comfortably and adequately conform to wound surfaces that are often irregular in contour. A dressing having such an inflexible or rigid structured material or wound contact layer can cause unnecessary pain and discomfort to a patient.

In WO 2006/052839 a vacuum wound dressing is described which is a fibrous blend or fibrous material that forms a cohesive gel when wetted with wound exudate. The dressing is in the form of a non-woven fibrous mat.

A wound dressing for use in vacuum wound therapy preferably has some or all of the following characteristics and properties:
  it is porous to allow exudate to flow;
  it has pores or holes to enable the underlying tissue to feel the effects of tissue strain;
  it can be easily folded or scrunched to fill the wound site;
  if fibrous, it has minimal fibre loss into the wound;
  it presents the same material properties to the side of the wound as it does to the wound bed so that the wound contact surface is consistent over the whole wound;
  it resists tissue ingrowth;
  it has sufficient wet strength to facilitate easy removal;
  it does not exert pressure on the wound bed on absorption of exudate;
  it is suitable for a range of sizes of wound and for various shapes and depths;
  it has minimal bioadhesion to minimise disruption to the wound bed on removal;
  it imposes beneficial strain on the tissue when suction is applied to it.

We have found that it is possible to provide a gel-forming wound dressing with many of the above desirable properties and which overcomes some of the problems of tissue ingrowth identified above while filling the wound and allowing exudate to flow out of the wound site when a vacuum is applied.

Accordingly the invention provides a wound dressing for use in vacuum wound therapy comprising a wound contact layer which is an open structure comprising a yarn which comprises gel-forming filaments or fibres, the structure having a porosity which allows exudate to flow through it.

It has been found that strain imposed on the tissue by the vacuum is believed to stimulate new tissue growth and assist healing. The porosity present in the open structure of the dressing according to the invention is believed to facilitate the application of strain to the tissue of the wound.

The open structure can be in the form of a net knitted, woven or embroidered from a yarn comprising gel-forming filaments or fibres. By the term yarn is meant a thread or strand of continuous filament or staple fibres. Alternatively the open structure can be first knitted, woven or embroidered from a textile yarn which is then chemically modified to impart gel-forming properties to it. For instance, the yarn can be a cellulose yarn which is knitted or woven to form the open structure and is then chemically modified to give the fibres greater absorbency and gelling properties.

By gel forming fibres is meant hygroscopic fibres which upon the uptake of wound exudate become moist slippery or gelatinous and thus reduce the tendency for the surrounding fibres to adhere to the wound. The gel forming fibres can be of the type which retain their structural integrity on absorbtion of exudate or can be of the type which lose their fibrous form and become a structureless gel. The gel forming fibres are preferably spun sodium carboxymethylcellulose fibres, chemically modified cellulosic fibres, pectin fibres, alginate fibres, chitosan fibres, hyaluronic acid fibres, or other polysaccharide fibres or fibres derived from gums. The cellulosic fibres preferably have a degree of substitution of at least 0.05 substituted groups per glucose unit. The gel forming fibres preferably have an absorbency of at least 2 grams 0.9% saline solution per gram of fibre (as measured by the free swell absorbency method BS EN 13726-1:2002 Test methods for primary wound dressings—Part 1: Aspects of absorbency, Method 3.2 free swell absorptive capacity).

Preferably the gel forming fibres have an absorbency of at least 10 g/g as measured in the free swell absorbency method, more preferably between 15 g/g and 25 g/g.

The dressing may for instance comprise non gel forming fibres and in particular textile fibres such as Tencel, cotton or viscose and may comprise lycra or other elastic fibre. Preferably the textile fibres have an absorbency of less than 10 g/g as measured by the free swell method and more preferably less than 5 g/g.

The pore size of the dressing in part determines the strain placed on the wound when suction is applied. The strain is also determined by the uniformity of the dressing over the area treated. The maximum strain and the uniformity of its application will therefore depend not only on the pore sixe of the open structure but also on the linear density of the yarn used to make the dressing. Maximum strain can be achieved by increasing the pore size or increasing the yarn linear density. Uniformity is increased by decreasing the pore size and decreasing the yarn linear density. We have found that acceptable strain is placed on the wound where the structure preferably has a pore size of between 0.5 mm$^2$ to 5.0 mm$^2$, more preferably between 3.0 mm² to 4.0 mm² and the yarn has a linear density of 20 tex to 40 tex.

The open structure can be in the form of a net with yarn joined at intervals to form a set of meshes or the open structure can be knitted with a pore sizes as mentioned above.

An advantage of such an open structure is that it is easily folded or crumpled to fit the wound and pack the wound site. Due to the structure, the dressing still allows exudate to pass through it when a vacuum is applied to the wound even though the dressing may not be co-planar with the wound bed. The conformability of the open structure allows all parts of the wound to be contacted with a similar dressing structure so that for instance the sides of the wound are contacted by the open structure as well as the wound bed.

In a further embodiment the invention provides a device for vacuum wound therapy comprising a wound dressing which is an open structure comprising a yarn of gel-forming filaments or fibres, the structure having a porosity which allows exudate to flow through it;
  a source of vacuum situated to be separated from the wound bed by the wound dressing; and
  a vacuum sealing layer covering the wound dressing and adapted to retain relative vacuum in the wound contact layer.

The open structure of the dressing of the invention can be made by first forming a yarn of gelling fibres. This may be done in various ways. For example gel forming fibres, which are for instance any of those mentioned above or can be modified cellulose, or carboxymethyl cellulose or alginate, can be spun into yarns comprising various blends of gel-forming staple fibres and textile fibres. The spinning may be done by first carding the fibres in the blend and spinning a yarn from the carded blend.

We have found that particularly suitable yarns can be formed by rotor spinning or open end spinning. In such a process, staple gel-forming fibres are blended with textile fibres and carded to produce a continuous web. The web is condensed to produce a card sliver and then rotor spun. In rotor spinning, a high speed centrifuge is used to collect and twist individual fibres into a yarn. The yarns produced from this technique have the characteristics of sufficient tensile strength to enable them to be further processed using knitting or weaving machinery.

A further embodiment of the invention provides a process for making a yarn comprising gel-forming fibres comprising the steps of:
  blending staple gel-forming fibres optionally with textile fibres;
  carding to form a continuous web;
  drawing the web to produce a sliver and rotor spinning to produce a yarn.

Yarns produced by this method preferably comprise from 30% to 100% by weight gel-forming fibres and 0% to 70% by weight textile fibres. More preferably the yarns comprise from 50% to 100% by weight of gel-forming fibres with the balance of textile fibres and most preferably from 60% to 100% by weight of gel-forming fibres.

The fibres present in the spun yarn preferably have a staple length of 30 to 60 mm, more preferably 40 to 55 mm and most preferably 45 to 55 mm.

A yarn made according to the processes of the present invention need not contain textile fibres enabling structures to be produced which consist wholly of gel-forming fibres.

A gelling yarn can be produced using a spun yarn consisting of natural cellulose fibres or solvent spun cellulose staple fibres or a blend of cellulose fibres and other textile fibres or by using a filament yarn of solvent spun cellulose which is then converted to chemically modify the yarn to produce gelling properties. For example, Lyocell yarns can be used as a starting material and converted in a kier process to impart gel-forming behaviour to the yarn.

Yarns made according to the processes of the present invention preferably have a dry tensile strength of at least 10 cN/tex, preferably from 10 to 40 cN/tex and most preferably from 16 to 35 cN/tex as measured by British Standard ISO 2062 2009.

Alternatively the open structure of the dressing of the invention can be made by weaving using a textile yarn and the resulting fabric then converted to impart gel-forming behaviour to it to form an open structure of gel-forming fibres.

It is also possible to warp or weft knit an open structure using a textile yarn such as Lyocell and then convert the resulting fabric to make the wound dressing of the invention. Further it is possible to embroider an open structure in textile yarn onto a support film which is then removed for instance by washing and the resulting structure converted to form an open structure comprising a yarn of gel-forming fibres.

In a further aspect the invention provides a process for making an open structure or net of gel-forming fibres by:
  embroidering an open structure in a textile yarn on a soluble support film;
  removing the support film by dissolving it and converting the structure give gel forming characteristics to the yarn and to form a structure comprising a yarn of gel forming fibres.

A preferred method of converting the yarns or fabrics is described in WO 00/01425. For example the yarns or fabrics can be carboxymethylated by pumping a reaction fluid through the reaction vessel and therefore the cellulosic materials at 65° C. for 90 minutes. The reaction fluid is a solution of an alkali (typically sodium hydroxide) and sodium monochloroacetate in industrial denatured alcohol. After the reaction time, the reaction is neutralised with acid and washed before being dried in a laboratory oven for 1 hour at 40° C.

Preferred embodiments of the invention are illustrated in the drawings in which:

FIG. 3b shows the locking in of one yarn by another for the fabrics in FIG. 3a;

Figure 1:
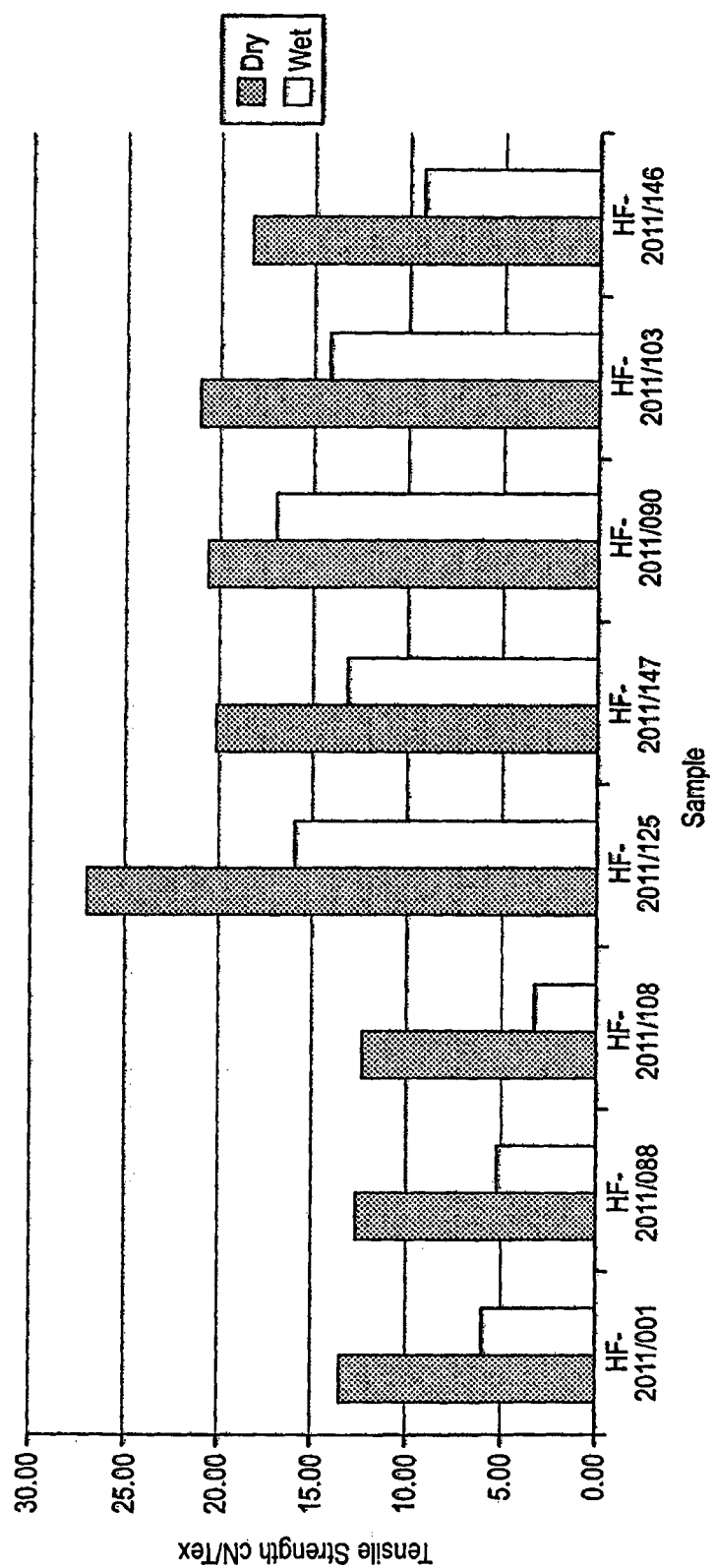
FIG. 1 is a graph showing tensile strengths for yarns according to the invention.

The invention is illustrated by the following examples.

EXAMPLE 1

Spinning Yarn from Staple Gel-Forming Fibres

Lyocell fibres and carboxymethyl cellulose staple fibres in blends of 50:50, 60:40 and 70:30 CMC:Lyocell were made by carding on a Trutzschler cotton card and spinning the resulting sliver at a twist of 650 turns/meter.

EXAMPLE 2

Converting a Textile Yarn to a Gel-Forming Yarn

Yarns were converted in the laboratory using a mini kier. In both trials, staple and filament lyocell yarns were converted. The yarns used for the conversion were staple 33 Tex Tencel®; HF-2011/090; and 20 Tex filament lyocell batches HF-2011/051 (trial 1) and HF-2011/125 (trial 2). Tencel® is a Lenzing owned, trademarked brand of lyocell and the Tencel® yarn used was a spun staple yarn. The filament lyocell was supplied by Acelon chemicals and Fiber Corporation (Taiwan) via Offtree Ltd.

The advantages of converting a yarn are that complete cones of yarn could potentially be converted in one relatively simple process, and the processing of gelling fibres is avoided, thus reducing the number of processing steps required and damage to the fibres.

Trial 1—Yarn Wrapped Around Kier Core

In this trial, Tencel® yarn was tightly wrapped around the perforated core of the kier using an electric drill to rotate the core and pull the yarn from the packages for speed. This meant that the yarn was wrapped tightly around the core under tension.

The yarn was converted by a process as described in WO 00/01425 in which carboxymethylation was carried out by pumping fluid through the kier and therefore the cellulosic materials at 65 C. for 90 minutes. The reaction fluid was a solution of an alkali (typically sodium hydroxide) and sodium monochloroacetate in industrial denatured alcohol. After the reaction time, the reaction was neutralised with acid and washed before being dried in a laboratory oven for 1 hour at 40 C.

The conversion was successful and both staple and filament gelling yarns were produced; HF-2011/103 and HF-2011/105 respectively. Due to the tight and uneven wrapping of the staple yarn around the core, it had to be removed using a scalpel which left multiple short lengths (approximately 14 cm) of the converted yarn.

Trial 2—Small Yarn Hanks

The aim of the second trial was to produce longer lengths of converted yarns for testing hence a small hank was made of each the staple and filament lyocell yarns by hand and these were placed between layers of fabric for the conversion.

The yarn was converted by placing the hanks in a kier and converting to form a gel-forming fibre yarn as described above for Trial 1.

The conversion was successful and both staple and filament gelling yarns were produced; HF-2011/146 and HF-2011/147 respectively.

Yarn Summary

|  | Sample | HF# |
|---|---|---|
| Gelling Yarns | 50:50 Spun staple gelling yarn | HF-2011/001 |
|  | 60:40 Spun staple gelling yarn | HF-2011/088 |
|  | 70:30 Spun staple gelling yarn | HF-2011/108 |
|  | Converted staple yarn (trial 1) | HF-2011/103 |

|  | Sample | HF# |
|---|---|---|
|  | Converted filament yarn (trial 1) | HF-2011/105 |
|  | Converted staple yarn (trial 2) | HF-2011/146 |
|  | Converted filament yarn (trial 2) | HF-2011/147 |
| Non-Gelling Yarns | Staple Tencel ® | HF-2011/090 |
|  | Filament lyocell (sample) | HF-2011/051 |
|  | Filament lyocell (bulk) | HF-2011/125 |

Results from Examples 1 and 2

With the exception of HF-2011/051, all of the yarns were tested for wet and dry tensile strength. Adaptations were made to the standard method BS EN ISO 2062:2009; "Textiles—Yarns from packages: Determination of single-end breaking force and elongation at break using constant rate of extension (CRE) tester". A Zwick tensile testing machine was used with a gauge length of 100 mm. The test uses a 100N or 20N liad cell to exert a constant rate of extension on the yarn until the breaking point is reached. Wet tensile testing was measured by wetting the samples with 0.2 ml of solution A in the central 3 to 4 cm of each yarn and leaving for 1 minute. The wetted sample was then placed in the jaws of the Zwick and clamped shut. Tensile strength was tested as the yarns produced need to be strong enough to withstand the tensions and forces applied during knitting, weaving and embroidery.

Tensile Strength

The results showed that all of the yarns were stronger when they were dry than when they were wet, with HF-2011/108, the 70:30 gelling yarn, showing the largest proportional strength decrease.

Of the yarns tested, HF-2011/108 was the weakest yarn both when wet and dry with tensile strengths of 12.4 and 3.4 cN/Tex respectively, despite containing 30% lyocell fibres. As this was the weakest yarn, but it was successfully weft knitted; HF-2011/120 and woven; HF-2011/169 into fabrics, it is believed that all of the other yarns would also be strong enough to be converted into fabrics.

Both approaches successfully produced gelling yarns.

EXAMPLE 3

Producing Open Structures from Gel-Forming Yarn

A yarn was produced with a 2/12 s worsted count consisting of 60% CMC fibres and 40% viscose fibres, each with a staple length of ~40 mm and the fibres were blended at the fibre stage. The yarn was produced using a worsted system and two 12 count strands were plied together. When dry, the yarn felt soft and the plying was clear as the two strands wrapped around each other. On wetting with Solution A, the yarn gelled and swelled to form a thicker yarn, and the plying became more pronounced.

A sample was made using this yarn on a warp knitting/stitch bonding machine and was hydrated with Solution A.

Figure 2:
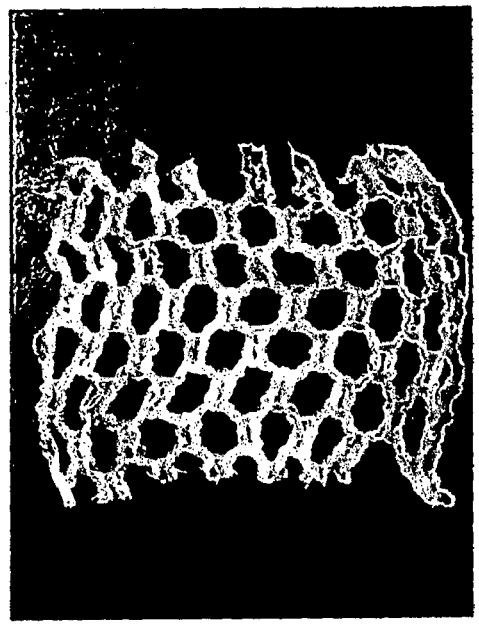
FIG. 2 shows open structures produced from a yarn comprising gel forming fibres in a relaxed, slightly stretched out and wet and slightly stretched out state.
Figure 2:
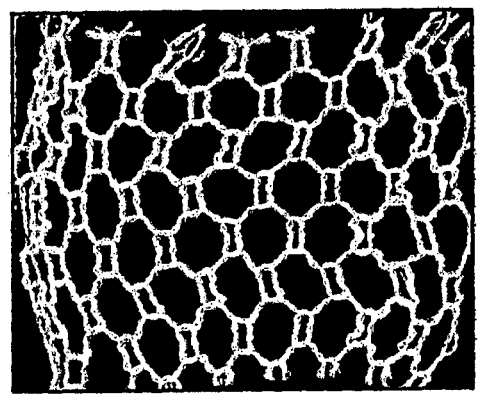
Figure 2:
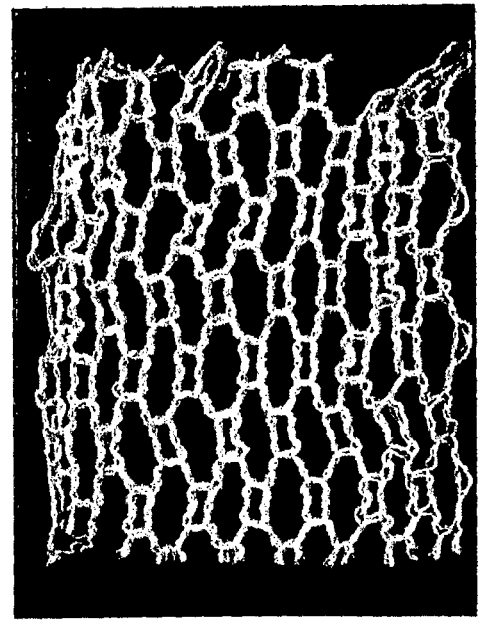
Figure 3A:
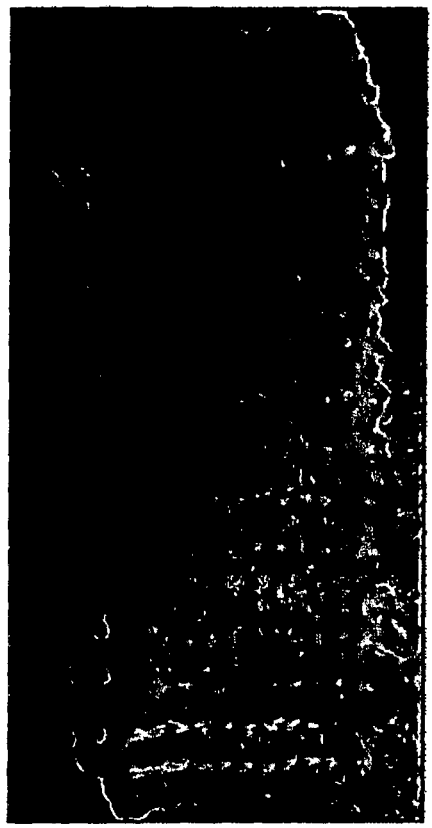
FIG. 3a shows a fabric knitted using Tencel warps and weft insertion of a yarn according to the invention in both dray and wet states.
Figure 3A:
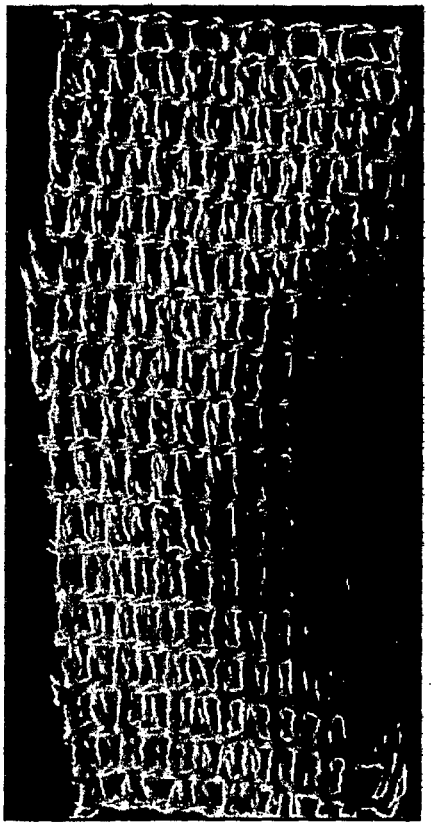
Figure 3B:
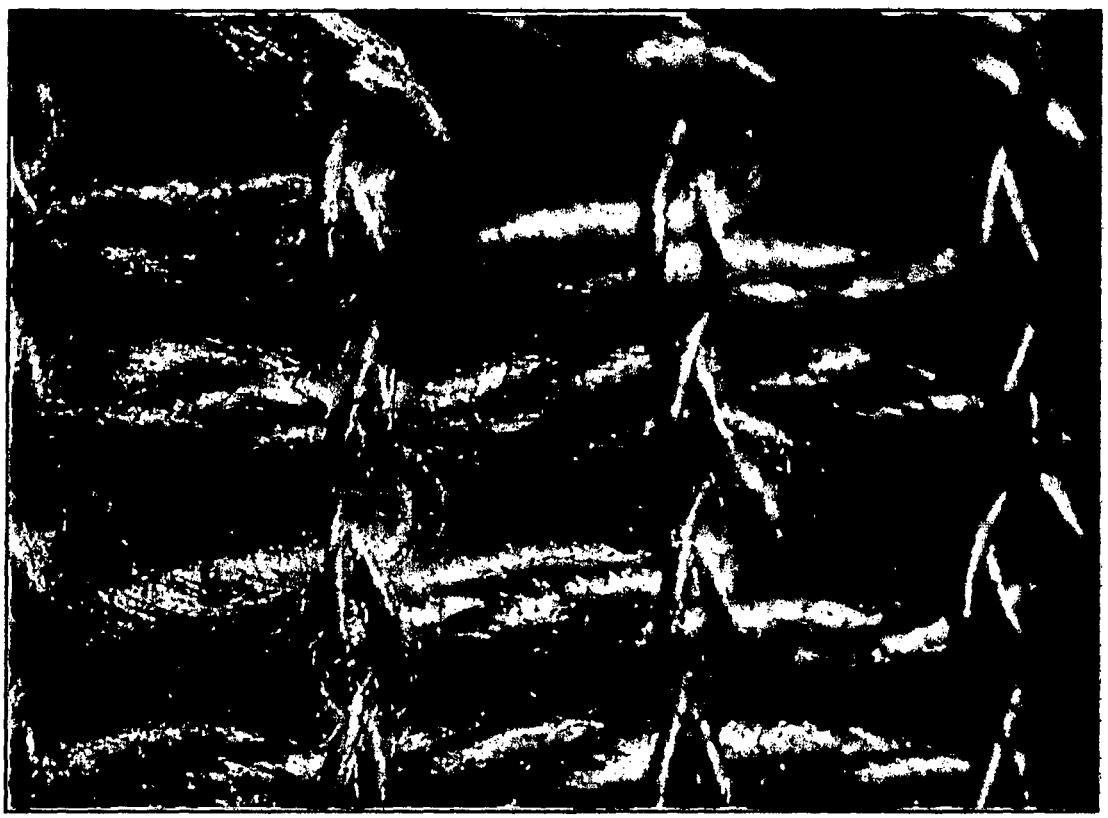
Figure 4:
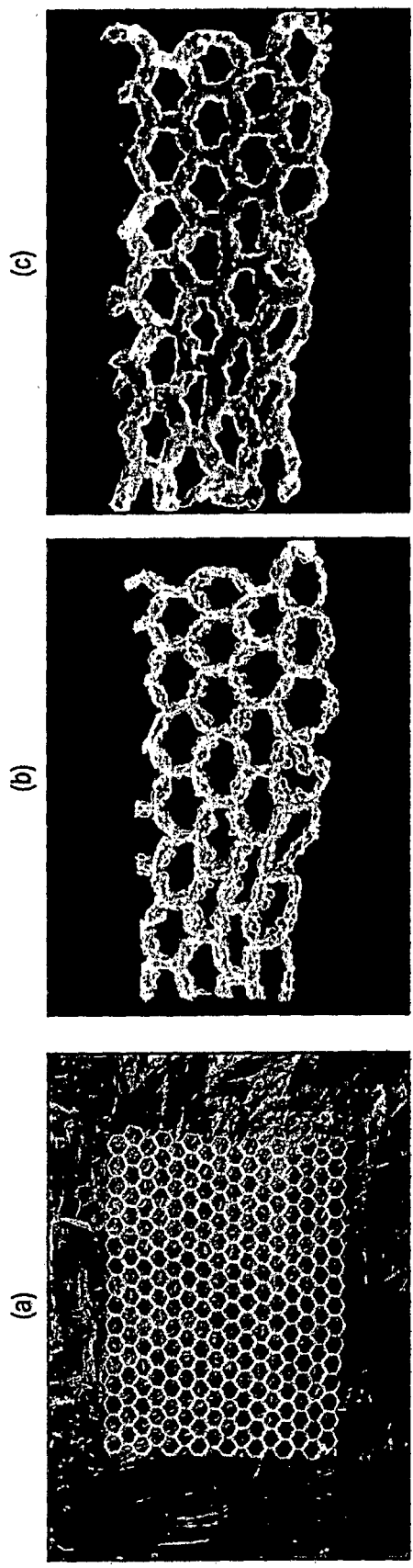
FIG. 4 shows an open structure produced by embroidering a textile yarn on a film, (a) showing the embroidered two layered structure on a film, (b) showing the converted dry structure and (c) showing that structure wet.

The sample structure was knitted with Tencel warp yarns and gelling yarn wefts in a net-like arrangement, which is especially visible when the structure is opened by gentle stretching, as shown in FIG. 2. On wetting the structure gels slightly and feels wet but it holds its open shape well.

EXAMPLE 4

A yarn comprising gel forming fibres was produced by the method of example 3. Using this yarn a fabric was knitted using Tencel warps and gelling yarn weft insertion. The weft yarns were inserted in such a way that they became locked in due to the pattern of knitting. This material has the weft yarn path notation of 0-1/1-1/1-2/2-3/3-2/2-1/1-2//. The material felt quite thin and when wet, it gels but seems to hold fluid on its surface.

EXAMPLE 5

Producing Open Structures from a Textile Yarn

Using a Tajima TMEX-C1201 embroidery machine fabrics were produced on a PVA film from lyocell thread (on the bobbin and as the top thread).
Thread=Gütermann 120 Tex lyocell thread from Tony Slade (T.S. Sewing Supplies)
Software=Wilcom ES
Programme name=honeycomb
Number of stitches=12,369 per 2 layers
Backing film=Soluble PVA film
Speed used=1200 rpm The film was removed by washing in warm tap water in a sink using lots of agitation until the film looked to have been removed. The samples were air dried on the bench The fabrics were converted by a process as described in WO 00/01425 and detailed in Example 2.

EXAMPLE 6

Warp Knitting to Produce a Locked in Structure.

Figure 5:
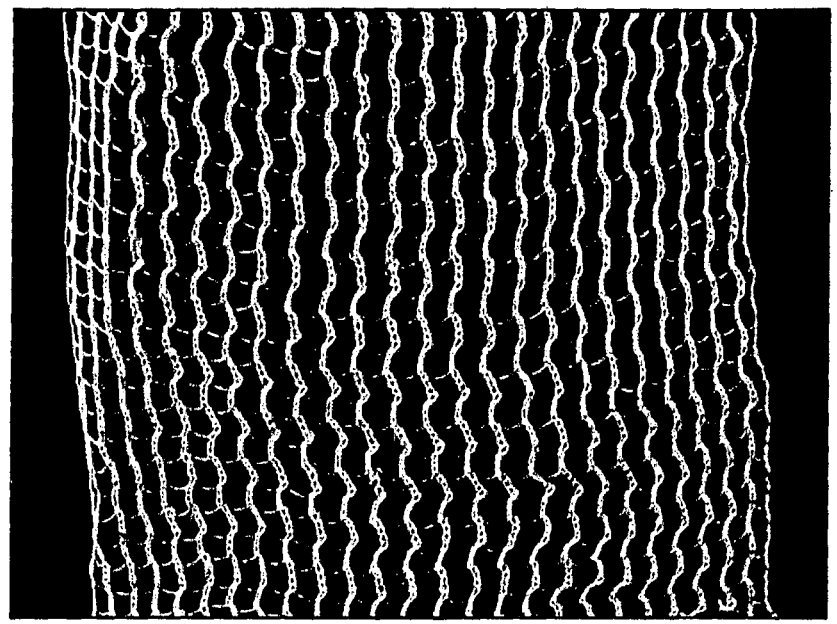
FIG. 5 shows a locked in a warp knitted structure produced using HF-2011/250.
Figure 6:
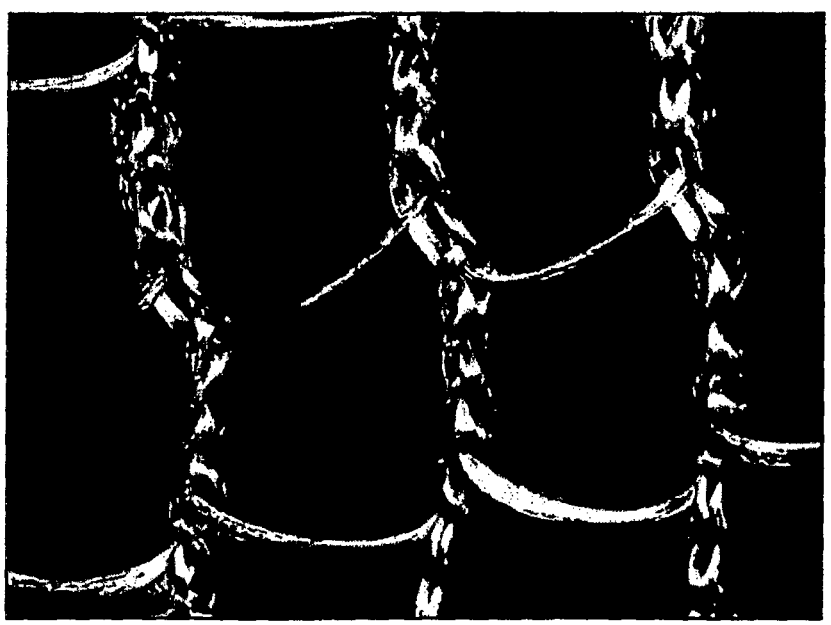
FIG. 6 shows a microscope image of FIG. 5 showing connecting yarns forming stitches within the pillar stitch.

To produce a fully locked in structure, a warp knitted fabric without any weft inlays is preferred. In the following example (FIG. 5) a fabric has been formed from a set of 4 pillar stitches, the yarn then underlaps to the adjacent set of pillar stitches and continues to form pillar stitches on this needle before underlapping back to the initial needle. Eg a typical yarn path notation for the simplest type of this fabric would be 0-2/2-1/2-1/2-0/0-1/0-1//. By using 2 sets of warp ends within one set of chain stitch alternating the yarn used for each stitch stops the structure being able to be unravelled easily. This structure could be complicated by using more needles within the design or using addition warp beams to underlap in opposite directions. The fabric produced is a locked in structure as the each knitted stitch is secured by a knitted stitch of another yarn end stopping the structure from unravelling and the threads going perpendicular to the pillar stitches also form loops within the structure, as shown in FIG. 6, ensuring that these are locked in.

EXAMPLE 7

Weaving

Open plain weave structures have been produced on a Northrop loom, using a gelling yarn previously described, HF-2011/108 to produce fabric HF-2011/169. And by using a Tencel spun yarn HF-2011/090 and converting at the fabric stage, to produce fabric HF-2011/136. The structure uses a warp density of 7.8 ends/cm and a weft density of 5.5 picks/cm.

Figure 7:
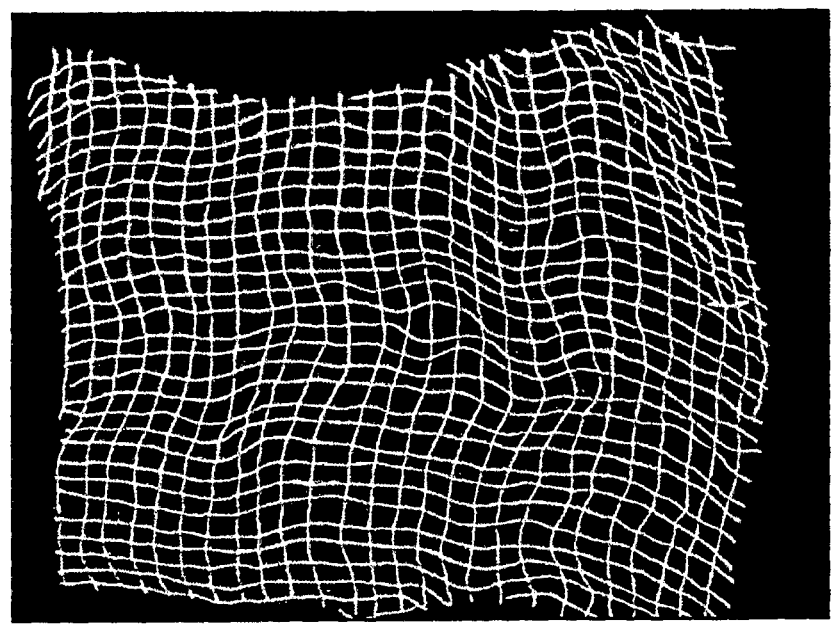
FIG. 7 shows a converted woven structure in a dry state.
Figure 8:
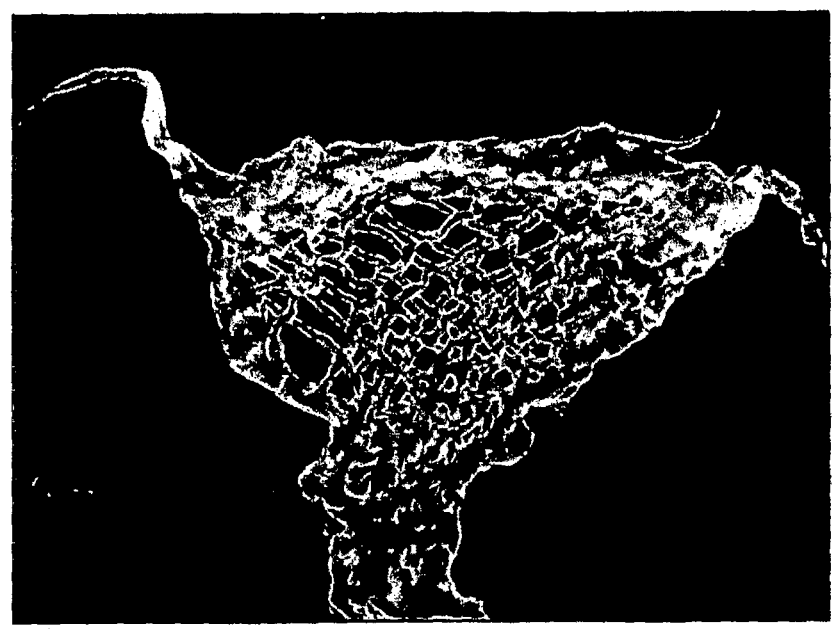
FIG. 8 shows the structure from FIG. 7 but wet.

FIG. 7 shows HF-2011/136, the sample converted at the fabric stage using the lab conversion process as previously described. This produced an open structure that is thin and flexible in its dry form. When wet this structure is less stable and bunches, but forms a gelled structure as shown in FIG. 8.

EXAMPLE 8

To produce a locked in woven sample, leno weaving is used. Leno weaving is a form of weaving in which warp threads are made to cross one another between the picks. As the warp yarns cross one another they are able to hold the weft yarns in place so little movement occurs within the structure. When the sample is cut theoretically the yarns should not be able to be removed as the free end is held in place by multiple warps within the rest of the structure. The leno can be applied to all or some of the yarns within the fabric.

The invention claimed is:

1. A wound dressing for use in vacuum wound therapy comprising
    a wound contact layer comprising an open structure in a form of a net comprising a spun yarn comprising a blend of gel-forming filaments or fibres and textile fibres, the net having a pore or mesh size from 0.5 mm$^2$ to 5.0 mm$^2$ that allows exudate to flow through the net, wherein the yarn has a linear density of 20 tex to 40 tex, wherein the yarn has a dry tensile strength of at least 10 cN/tex, wherein the textile fibers have an absorbency of between 5 g/g and 10 g/g as measured by the free swell method, and wherein the blend of gel-forming filaments or fibres and textile fibres includes only one type of gel-forming filaments or fibres.

2. A wound dressing as claimed in claim 1 wherein the net is knitted, woven, or embroidered.

3. A wound dressing as claimed in claim 1 wherein the pore or mesh size of the net is between 3.0 mm$^2$ to 4.0 mm$^2$.

4. A wound dressing as claimed in claim 1 wherein the net is knitted.

5. A wound dressing as claimed in claim 1 wherein the net is joined at intervals to form a set of meshes.

6. A wound dressing as claimed in claim 1 wherein the yarn comprises 30% to 100% by weight gel-forming filaments or fibres.

7. A wound dressing as claimed in claim 1 wherein the net comprises 50% to 100% by weight gel-forming filaments or fibres.

8. The wound dressing of claim 1 wherein the yarn has a dry tensile strength from 10 cN/tex to 40 cN/tex.

9. The wound dressing of claim 1 wherein the spun yarn comprises a blend of the gel-forming filaments or fibres and the textile fibres in a ratio of 60:40 to 70:30.

10. The wound dressing of claim 1, wherein the pore or mesh size of the net facilitates application of strain to tissue through pores or mesh of the net to stimulate tissue growth when a vacuum of at least 0.4 atm is applied by a vacuum source to the wound dressing such that a relative vacuum is retained in the wound dressing.

11. A device for vacuum wound therapy comprising:
    a wound dressing comprising an open structure in a form of a net comprising a spun yarn comprising a blend of gel-forming filaments or fibres and textile fibres, the net having a pore or mesh size from 0.5 mm$^2$ to 5.0 mm$^2$ that allows exudate to flow through the net, wherein the yarn has a linear density of 20 tex to 40 tex, wherein the yarn has a dry tensile strength of at least 10 cN/tex, and wherein the blend of gel-forming filaments or fibres and textile fibres includes only one type of gel-forming filaments or fibres;
    a source of vacuum situated to be separated from a wound bed by the wound dressing; and
    a vacuum sealing layer separate from the wound dressing that covers the wound dressing and is adapted to retain relative vacuum in the wound dressing,
    wherein the pore or mesh size of the net facilitates application of strain to tissue through pores or mesh of the net to stimulate tissue growth when a vacuum of at least 0.4 atm is applied by the source of vacuum to the wound dressing such that the relative vacuum is retained in the wound dressing by the vacuum sealing layer.

12. A device as claimed in claim 11 wherein the net is knitted, woven, or embroidered.

13. A device as claimed in claim 11 wherein the yarn comprises 30% to 100% by weight gel-forming filaments or fibres.

14. A device as claimed in claim 11 wherein the net comprises 50% to 100% by weight gel-forming filaments or fibres.

15. The device of claim 11 wherein the yarn has a dry tensile strength from 10 cN/tex to 40 cN/tex.

16. The device of claim 11 wherein the spun yarn comprises a blend of the gel-forming filaments or fibres and the textile fibres in a ratio of 60:40 to 70:30.

17. The device of claim 11, wherein the textile fibers have an absorbency of between 5 g/g and 10 g/g as measured by the free swell method.

18. A wound dressing comprising a wound contact layer comprising an open structure in a form of a net comprising a spun yarn comprising a blend of gel-forming filaments or fibres and textile fibres, the net having a pore or mesh size from 0.5 mm$^2$ to 5.0 mm$^2$ that allows exudate to flow through the net, wherein the yarn has a linear density of 20 tex to 40 tex, wherein the yarn has a dry tensile strength of at least 10 cN/tex, and wherein the blend of gel-forming filaments or fibres and textile fibres includes only one type of gel-forming filaments or fibres.

19. The wound dressing of claim 18 wherein the yarn has a dry tensile strength from 10 cN/tex to 40 cN/tex.

20. The wound dressing of claim 18, wherein the pore or mesh size of the net facilitates application of strain to tissue through pores or mesh of the net to stimulate tissue growth when a vacuum of at least 0.4 atm is applied by a vacuum source to the wound dressing such that a relative vacuum is retained in the wound dressing.

\* \* \* \* \*